United States Patent
Wiets et al.

(10) Patent No.: US 9,980,783 B2
(45) Date of Patent: May 29, 2018

(54) BONE REPOSITIONING BASED ON AN AUTOMATED ASSIGNMENT

(71) Applicants: Michael Wiets, Langensendelbach (DE); David Winneberger, Nürnberg (DE)

(72) Inventors: Michael Wiets, Langensendelbach (DE); David Winneberger, Nürnberg (DE)

(73) Assignee: Siemens Aktiengesellschaft, München (DE)

( * ) Notice: Subject to any disclaimer, the term of this patent is extended or adjusted under 35 U.S.C. 154(b) by 99 days.

(21) Appl. No.: 15/141,672

(22) Filed: Apr. 28, 2016

(65) Prior Publication Data

US 2016/0321807 A1 Nov. 3, 2016

(30) Foreign Application Priority Data

Apr. 28, 2015 (DE) .................. 10 2015 207 727

(51) Int. Cl.
*G06K 9/00* (2006.01)
*A61B 90/00* (2016.01)
(Continued)

(52) U.S. Cl.
CPC .......... *A61B 90/361* (2016.02); *G06T 7/0012* (2013.01); *G06T 7/33* (2017.01);
(Continued)

(58) Field of Classification Search
CPC ........ A61B 90/361; G06T 2207/10116; G06T 2207/30008; G06T 7/0012; G06T 7/33
See application file for complete search history.

(56) References Cited

U.S. PATENT DOCUMENTS

| | | | | |
|---|---|---|---|---|
| 2008/0004517 | A1* | 1/2008 | Bhandarkar | A61B 90/36 600/407 |
| 2013/0314440 | A1* | 11/2013 | Simon | G06T 7/0014 345/629 |
| 2015/0125033 | A1* | 5/2015 | Murphy | G06T 7/251 382/103 |

FOREIGN PATENT DOCUMENTS

| DE | 102006048451 A1 | 4/2008 |
|---|---|---|
| DE | 102007034221 A1 | 4/2008 |

OTHER PUBLICATIONS

"Operationen und Prozeduren der vollstationären Patientinnen und Patienten in Krankenhäusern. Gliederungsmerkmale: Jahre, Behandlungsort, Alter, Geschlecht", Gesundheitsberichterstattung des Bundes / Jun. 11, 2014.
(Continued)

*Primary Examiner* — Tom Y Lu
(74) *Attorney, Agent, or Firm* — Lempia Summerfield Katz LLC

(57) ABSTRACT

A method and a control module for calculating and displaying result data based on at least one medical image, which has been captured by an imaging device, are provided. At least one image is captured by the imaging device in a digital format with a plurality of bone fragments. Subsequently, a segmentation method is applied to the captured image for identification of the bone fragments contained in the image. Thereafter, a fragment-matching algorithm is executed on the segmented bone fragments for calculation of result data. The result data includes instruction data for assembling at least a part of the bone fragments, which is output on the monitor in a configurable format.

15 Claims, 2 Drawing Sheets

(51) Int. Cl.
    *G06T 7/00*           (2017.01)
    *G06T 7/33*           (2017.01)

(52) U.S. Cl.
    CPC ............... *G06T 2207/10116* (2013.01); *G06T 2207/30008* (2013.01)

(56) References Cited

OTHER PUBLICATIONS

Goldberg, David et. al.: "A Global Approach to Automatic Solution of Jigsaw Puzzles", in: SCG 02: Proceedings of the eighteenth annual symposium on Computational Geometry, pp. 82-87, New York, NY, USA, 2002.

Kong, Weixin et. al.: "On Solving 2D and 3D Puzzles Using Curve Matching", in: Proc. of the IEEE Conference on Computer Vision and Pattern Recognition, Hawaii, 2001.

Schafleitner, Christian: "Problematik eines Puzzlespiels aus der Sicht der digitalen Bildverarbeitung", Bakkalaureatsarbeit, Nr. 03-1-0238-058-A, Fachhochschul-Bakkalaureatsstudiengang Medientechnik und—design in Hagenberg, Feb. 2006.

* cited by examiner

BONE REPOSITIONING BASED ON AN AUTOMATED ASSIGNMENT

This application claims the benefit of DE 10 2015 207 727.6, filed on Apr. 28, 2015, which is hereby incorporated by reference in its entirety.

BACKGROUND

The present embodiments are in the fields of medical imaging and automation and information technology. The present embodiments relate to a calculation method for result data during the assignment of bone fragments in the operative environment.

With complex bone fractures, one medical task consists of identifying the bone fragments and assigning the bone fragments to one another so that the bone may be reconstructed as well as possible within the framework of a subsequent operation. To do this, a number of measures, which have previously been performed manually or were not possible, are to be taken in advance.

A preparatory measure for an operative intervention includes finding an optimum and correct positioning for the individual bone fragments. This task may be understood as searching for a solution to a positioning problem of individual parts.

SUMMARY AND DESCRIPTION

The scope of the present invention is defined solely by the appended claims and is not affected to any degree by the statements within this summary.

One approach to a solution for the present embodiments is based on using knowledge from the field of puzzle research, entirely alien to the field of medicine, and modifying the field of puzzle research such that puzzle research is able to be employed to resolve the medical positioning task discussed here.

The use of algorithms for automatic solution of puzzle tasks is known from the field of puzzle research. Such an algorithm is discussed in greater detail in the article "A global Approach to Automatic Solution of Jigsaw Puzzles," by Goldberg D., Malon C., Bern M. In this article, the solution is based on specific assumptions (e.g., that the puzzle has a rectangular outline and that the puzzle pieces each have 4 neighbors), which however, are not applicable to other fields, such as the field of medicine, since other circumstances (e.g., irregular outline, more than 4 neighbors, etc.) predominate here. Thus, the algorithms known in the field of puzzle research may not be applied to the present field of medical technology without comprehensive adaptations.

The present embodiments may obviate one or more of the drawbacks or limitations in the related art. For example, an automated method with which an automatic solution for calculating result data for a repositioning and assignment of bone fragments may be provided with the aid of an imaging device is provided.

According to a first aspect, a method for calculation and output of result data based on at least one medical image that has been acquired by an imaging device includes carrying out a medical imaging method using the imaging device for acquiring at least one image (e.g., an image sequence; "the acquired image" is often just referred to below) in a digital format with a plurality of bone fragments. The method also includes applying a segmentation method based on the acquired image for identification of the bone fragments contained in the image, and carrying out a fragment-matching algorithm on the segmented bone fragments for calculating result data. The result data contains instruction data for joining together at least a part of the bone fragments. The method includes outputting the result data in a configurable format.

The method is implemented by computer and is carried out as a preparatory measure of a medical operation, which is performed with imaging support. The method may not require any user inputs and may be carried out fully automatically. The method is a calculation method and serves to output result data, which may be output to a graphical user output or to a loudspeaker. The format in which the result data is output is configurable. In a configuration phase, a setting may be made as to which format is to be used here. Thus, the result data and/or the instruction data may be output not only in a visual format (e.g., graphical or textual) but also in an acoustic format or as a light signal (e.g., by illumination elements such as LEDs and not on a screen or as a visual signal on a display device).

The method is based on the creation of at least one image or a sequence of images in a digital format. In one embodiment, a mobile C-arm is used for this purpose as an x-ray device. As an alternative, however, computed tomographs or stationary, permanently-installed, x-ray-based systems may be used. As an alternative, another modality may be involved (e.g., a magnetic resonance tomograph, an ultrasound device, classical x-rays).

The segmentation method is an automatic image processing method, with which the individual bone fragments, which are shown on the acquired image, are identified. For this identification, algorithms for pattern recognition are executed. In an embodiment, a flood-filling algorithm may be employed. The flood-filling algorithm additionally labels the parts or bone fragments (e.g., marks and if necessary consecutively numbers) and/or assigns surrounding anatomical structures (e.g., the maxilla, the lamina perpendicularis, or the individual face bones). To carry out the segmentation method, there may also be access to a database in which anatomical part structures for reconciliation with the acquired image data are stored. The result of the segmentation method may then be verified in an additional method step by reconciling the result with stored datasets. Metadata for further checking (e.g., with respect to size and/or location of the fragment or bone or of the anatomical structure) may be used. The segmentation method may be based on a two-dimensional or three-dimensional pattern recognition.

The format in which the result data is output may be configured. This provides that not only the result data may be output in different text formats, but rather, the result data may be provided in a different way (e.g., in a visual format, an acoustic format, and/or as light signals). This proves very helpful, especially when used in the medical environment, since the doctor is then diverted as little as possible or not at all by the cognitive acquisition of the result data. The result data (e.g., the instruction data) may include an instruction set or a type of "guide to repositioning by visual support." Information that identifies the fragment that is to be used first of all or next and how the fragment is to be placed against the existing bone edge is thus provided. Meta information may be included, that, for example, the fragments that are left over at the end may confidently be removed.

In a form of embodiment, the position and/or the movement of the surgeon's instruments may be "tracked" with a navigation system (e.g., by active or passive markers and a optical referencing system). Thus, the position and/or the movement of the surgical device may be detected and calculated in relation to the result data. Depending on where the device is moved to, a different signal may be output as instruction data in order to be able to provide device guidance. In this case, different variants are fundamentally able to be executed. A high-frequency acoustic signal may be output when the instrument approaches a detected target region, and a low-frequency signal may be output if the instrument is moved away from the target region. Another option includes correlating the proximity to the target region with the duration of the acoustic signal and outputting an acoustic signal, in the form of a long signal tone or a continuous tone, for a movement that is moving away from the target/bone segment and a shorter tone for a movement that is reaching the target/bone segment. Other configurations such as, for example, a series of tones of different length/duration or the output of light or illumination signals may be provided. The parts or bone fragments that are touched by a device may have colors assigned or may be provided with characters (e.g., Greek) or numbers. This assignment may either be carried out manually or automatically. In an advantageous and simple embodiment, a further variant may be provided according to a "traffic light principle." In this case, for example, a "red signal" counts as instruction signal for an "incorrect" bone segment, while a "green signal" represents a "correct" bone segment. The respective bone segment is selected in this case in relation to a specific intact or already fixed bone segment or a corresponding anatomical structure.

The fragment-matching algorithm is used for selection of bone segments in a specific order for the repositioning and joining together of the bone fragments where possible in an original position. The fragment-matching algorithm is thus also used, at least indirectly, for positioning of individual bone fragments. The fragment-matching algorithm is based on a feature-based matching method. A curve-matching algorithm may, for example, be employed. The pattern recognition is based on a 2D or a 3D pattern recognition. The 3D pattern recognition takes account of both the spatial position of both the bone fragment and also the target structure to which or onto which the bone fragment is to be fastened.

In a development, at least one parameter may be configured in advance of carrying out the method (e.g., a matching threshold value that identifies the degree to which a match between the bone fragments is to be obtained). This proves helpful in taking account of a different degree of fragmentation of the bones during repositioning. It may thus be set, for example, that, with a very high degree of fragmentation, in which the bones are heavily fragmented, the match may not be as great as for a low degree of fragmentation in which just a few large bone fragments are to be repositioned, which may be required to match to a high degree. This increases the flexibility of the method and the ability to adapt to different medical case situations.

As part of this application, a distinction is made between two different datasets: Instruction data and result data. The result data includes the instruction data. The result data identifies the solution of the fragment matching algorithm employed and specifies where which bone fragment is to be positioned in order to be able to re-establish the original anatomical situation as precisely as possible. The result data may be provided in the form of image data (e.g., as a kind of solved or assembled puzzle). The instruction data contains yet further information. The instruction data is the basis for a guidance in the positioning of the medical instruments. The instruction data contains commands for positioning the instruments with the respective bone fragments at the calculated point. The instruction data, as described above, may be output in acoustic and/or optical form. In a corresponding way, the result data may also be provided in a different way and in different formats (as described above in conjunction with the instruction data). The instruction data is calculated by, in an updated form in each case, an ACTUAL position of a fragment or of a surgical device (e.g., for holding and positioning the fragment) being acquired and reconciled with a calculated TARGET position in accordance with the result data.

In an embodiment of the method, the method has recourse to a database in which anatomical structures and substructures are kept, which may be assigned by a mapping method automatically to the segmented bone fragments. Thus, the quality of the bone fragment positioning method may be enhanced. In a development, there is provision for the system to be embodied as a self-learning system. In this case, the database is successively expanded by all acquired images, segmented bone fragments, and result data being stored automatically in the database. Instruction data is also stored. In this case, a further dataset that identifies whether the positioning suggestion (e.g., calculated with the result data) was successful or correct or could not be implemented may be acquired. This feedback for the result data is also stored in the database in order to be able to provide optimization for future cases. The feedback data may be acquired and stored, for example, by actuating a button on a user interface (e.g., "successful/unsuccessful").

In a further embodiment of the method, additionally and, for example, before use of the fragment-matching algorithm, a further act is carried out (e.g., image processing or an image modification measure). The image modification measure may include coloring-in the segmented bone fragments and/or the background. This act serves to recalculate the acquired image in order to use this as the basis for the fragment-matching algorithm, which may achieve better results with the newly calculated image. In one variant, the image modification measure may also be carried out before the segmentation method.

In one embodiment, the calculated result data is output. In one embodiment, this is done for a visual representation of the data on a display device. As an alternative or cumulatively, this may also be done by a loudspeaker for acoustic signals. In this case, the mode may represent the acoustic signal (e.g., content or tone level or tone duration) the proximity or distance to the TARGET position. With a visual representation of the result data, the respective bone fragment may be displayed with highlighted outlines and a calculated TARGET position for correct repositioning at existing bones. In such cases, landmark elements (e.g., important, central, easily-recognizable bones or anatomical anchor points that are easily recognizable both on the acquired image and also in the operative environment) may be used for easier orientation (even in highlighted form).

In a development, the method or system includes an optical tracking system that is referenced with the imaging device and thus has a common frame of reference with the imaging device. The optical tracking system includes a camera (e.g., a stereoscopic camera) to detect the current position of the instrument and overlay the current position of the instrument on the acquired image of the imaging device or to transmit the current position of the instrument into the device. Thus, a current instrument position (e.g., of an instrument that holds a specific bone fragment) may be reconciled with a calculated TARGET position (e.g., from the result data). This makes it possible to guide the instrument with optical and/or acoustic support of the instrument or indirectly guide the repositioning of the respective bone fragments.

As already stated in the introduction, the puzzle algorithms known from puzzle research may not be used without modification for the bone fragment positioning task, because other preconditions are to be taken into account here. Thus, the bone fragments, in an intended and original position, do not generally have a rectangular outline. The assumption that a fragment generally has four neighbors in each case does not apply. The number of neighbors may be any given number. In addition, fragments in a comminuted fracture may be heavily splintered and not have any clear outline, which makes it necessary both to adapt the segmentation algorithm and also a known puzzle algorithm. The principles of the puzzle algorithm known in the prior art are modified or expanded by the following aspects. An outline correction enables bone splinterings to be taken into account. In this case, there may be provision for an outline line to be detected (e.g., using automatic image processing methods). The detected outline line may then be modified with a mouse, for example, in order thus to be able to exclude parts of the fragment, for example. An anatomy mapping enables suitable account to be taken of the anatomical circumstances. A location correction enables account to be taken of specific positionings for part bone fragments. A start point correction makes it possible for a start point for the respective anatomical situations to be selected in the optimum possible way. In this case, an intact bone fragment that is large as possible is determined, and a suitable neighboring bone fragment is calculated. By contrast, known puzzle methods generally first begin with the outline (e.g., with the outer edge of the puzzle), which does not achieve the desired aim for application in medical technology. A configuration option for the degree of required match between the individual bone fragments may be provided. In this case, for example, the size of the bone fragment (e.g., 2 mm$^2$) that is to be taken into account for the repositioning task may be configured. A 3D expansion, which takes into consideration and calculates the spatial positioning (ACTUAL position and TARGET position) of the bone fragment in relation to the surrounding anatomy, may be provided. An interaction option may also be provided. In this case, the user may also manually position, rotate, and/or move a selected bone fragment, for which the TARGET position is obvious (e.g., for bones with quite specific shapes such as the malleolus in the ear). An abort criterion, which is determined, for example, as a result of the size or as a result of the shape may be provided. A long, pointed bone needle may not match.

The method may be employed in two different variants. The method may be operated in an interleaved mode, in which a fragment positioning phase and a search phase for the next bone fragment alternate in each case. In the fragment positioning phase, a part of the result data or instruction data is implemented for the respective bone segment in that the respective bone fragment is positioned at the calculated TARGET position. In accordance with the interleaved mode, each fragment positioning phase is followed by a search phase. In the search phase, at least one adjacent bone fragment is sought. Thus, in interleaved mode, the fragment positioning and the search phase alternate for a pre-specifiable number of bone fragments. The method may also be operated in a block mode. In block mode, the result dataset includes the positioning suggestions for all bone fragments, and outputs the suggestions. Following on from the completely executed search phase, the fragment positioning phase is executed (e.g., successively for all bone fragments). It is also possible to carry out a mixed form. In the mixed form, in the search phase, the result data may be jointly calculated and output for a number of bone fragments. This is then followed by the fragment positioning phase for the respective bone fragments. Once these are positioned, the next search phase for a predeterminable number of neighboring bone fragments may be carried out. This is repeated iteratively until such time as all bone fragments have been positioned. The mixed form has the advantage of enabling flexible reaction to the respective anatomical situations. Thus, it may be determined for very large fragments that a number of fragments may be positioned at the same time in one process, and thus, the search phase is carried out for a number of fragments, while for a plurality of small and sometimes difficult-to-position fragments, only one fragment after the other may be positioned before the next one is sought. The mixed form has the further advantage that perhaps fragments that have not previously fit anywhere may then be accommodated immediately. A disadvantage of the block method, however, is also that a new dataset will presumably be recorded in the meantime, and the algorithm is to run again, since there have been all sorts of movements caused by the positioning.

The fragment-matching algorithm may include a verification process, with which a calculated suggestion for positioning at least one bone fragment may be verified or rejected by the user. The user is provided with an input mask, in which the user may enter a verification signal. This may be done by clicking on a confirmation button. Only when the system has received a signal for the calculated suggestion will the suggestion be output as the result dataset.

The fragment-matching algorithm may be operated initially in a planning mode. In the planning mode, only one suggestion for positioning is created. On the basis of this suggestion, an overall positioning of all fragments is then calculated and displayed virtually, without a real bone positioning being carried out in vivo. The fragments are then displayed visually in a calculated TARGET position in each case in the form of a 3D model. If it transpires in this display that at least one bone fragment is incorrectly or wrongly positioned, the error may be corrected. To this end, the method may include backtracking. Backtracking is used for retroactive correction of already calculated result data and positioning suggestions. This proves to be sensible if at an advanced stage of the search/positioning, it turns out that already positioned bone fragments have been incorrectly positioned and are to be positioned again. Then, the previous positioning suggestions are to be reversed again so that the bone fragments may be set in another position.

In an embodiment, the fragment-matching algorithm may include a prioritization. The prioritization is used to define a relevance of the respective bone fragment. The high-priority fragments are processed first, while low-priority fragments may be processed later. As a rule, it is preset that larger fragments are assigned a higher priority.

Features, advantages or alternate forms of embodiment mentioned above are likewise also to be transferred to the other subject matter and vice versa. In other words, the physical subject matter (e.g., directed to a control module or system or to a computer program product) is developed with the features that have been described in conjunction with the method. The corresponding functional features of the method are embodied in such cases by corresponding physical modules (e.g., by hardware modules or microprocessor modules) of the systems or of the product and vice versa.

A control module (e.g., a controller) is also provided. The control module includes a segmentation module and a processor. The result and/or instruction data is output on an output unit, which may be embodied as a monitor, as an illumination element, or as a loudspeaker.

A computer program product, which is loaded or which may be loaded into a memory (e.g., a non-transitory computer-readable storage medium) of a computer, with computer program code for carrying out the method described in greater detail above when the computer program product is executed on the computer is provided.

A computer program with computer program code for carrying out all method acts of the method described above when the computer program product is executed on the computer is also provided. In this case, the computer program may be stored on a computer-readable medium.

DETAILED DESCRIPTION

The present embodiments relate to a computer-based method that may be used in the traumatology environment. In traumatology, comminuted fractures often occur in the region of the cranium. These are caused, for example, by bicycle or motorcycle accidents, falling face down, and also blows. In Germany each year, more than approximately 330,000 face bone fractures are treated or operated on and corrected. For example, in the area of maxillofacial surgery, there are currently hardly any technical aids available for reconstructing the highly complex fractures. A large market is involved in which today typically a mobile C-arm for digital 2D imaging is used. A reconstruction of a cranofacial fracture, and/or a number of fractures, which may include at least two, but also of up to thirty and more individual bone segments (in such case, the size of the individual pieces of bone sometimes amounts to less than a few square millimeters), lasts without sufficient imaging for several hours and is major "forceps work" (e.g., since the doctor must decide and manually test out which bone part matches another). In total, this provides a very long operation time, with all the risks and stresses for the patient associated therewith (e.g., correspondingly a long use of the devices (C-arm for imaging), of the operating theatre, and of the corresponding personnel). A further complicating factor is that the surrounding tissue has become massively swollen and bloodied by the injury, which makes it even harder to search for the matching pieces of bone. Not all bone segments may be assigned, which puts the result of the operation in a strongly negative light for the patient. The OP result is typically only checked after the operation with the aid of a CT scan. Should it be established here that something does not match, the patient is to be operated on a further time. This results in increased costs for the clinic and great stress for the patient.

Figure 1:
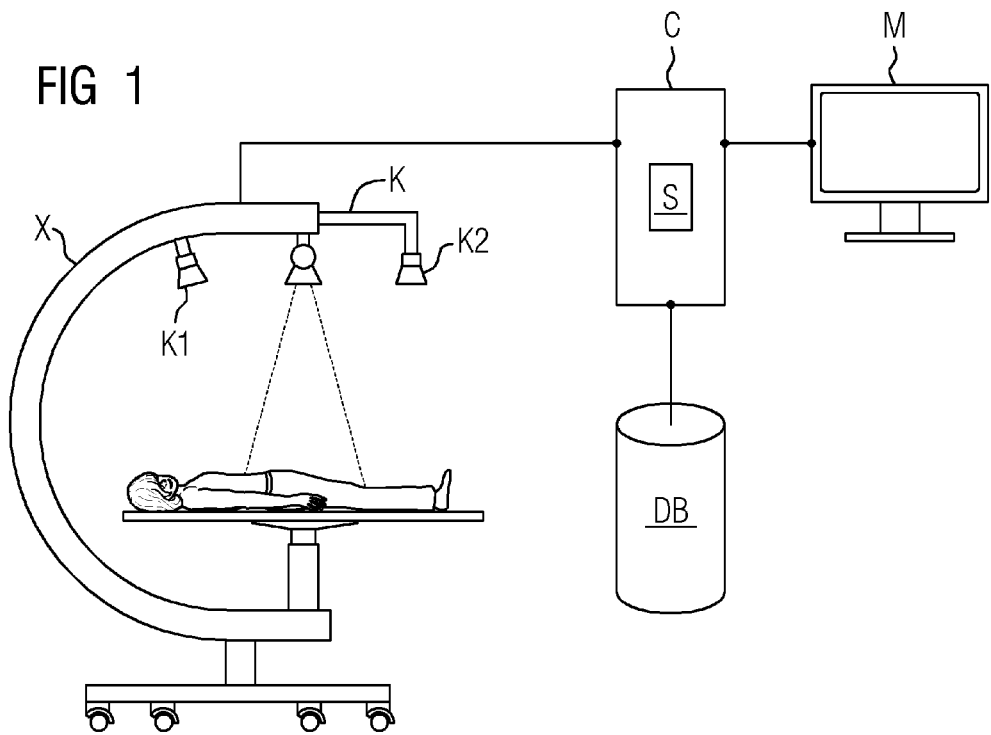
FIG. 1 shows a schematic overview diagram of a calculation unit in accordance with an embodiment.

The present embodiments are explained in greater detail below with reference to FIG. 1.

A mobile or stationary C-arm X is used as the imaging device in order to create at least one image or a series of images or a number of image segments in a digital format (e.g., in a Digital Imaging and Communications in Medicine (DICOM) format. To capture an optical image, a stereoscopic camera system K is provided, which has at least two optically spaced camera lenses K1, K2. The camera system K is disposed on the C-arm X or is provided as a separate component. When the camera system K is disposed on the C-arm X, the camera system K is referenced with the C-arm by a registration method, so that the optical images captured with the camera system K may be assigned to the images captured with the C-arm X. The C-arm X and the camera system K are connected via a data interface (e.g., wireless or wired) to a computer C, which includes a control module S. The computer C may exchange data with a database DB. A monitor M, which is used for displaying images and data, may be connected to the system.

For a fractured bone (e.g., with multiple fractures), the individual bone fragments F are to be positioned with automated support so that the bone may be reconstructed as well and as completely as possible. In such cases, the individual fracture parts F (e.g., $F_1$, $F_2$, $F_3$) may initially be recorded with the aid of intra-operative 3D imaging 1 (e.g., syngo DynaCT, syngo DynaCT Micro). These may subsequently be segmented automatically with a segmentation method 2 and the individual parts shown differently on the monitor M in color or by other methods (e.g., numbered or identified by symbols). With the aid of a fragment matching algorithm 3 described in greater detail below, the individual parts, in a similar way to a puzzle solution, are automatically assembled. The way in which the solution is obtained may be shown graphically on the monitor M, so that the solution is verifiably achievable for the surgeon.

In accordance with an embodiment, initially, a large intact bone section is specified or defined. In the best case, this is the edge of the intact cranium bone. The fragment matching algorithm 3 attempts to place free bone segments $F_1$, $F_2$, . . . $F_n$ suitably on the intact bone segment in turn, by rotation around all three centroidal axes and by changing and moving the free bone segments $F_1$, $F_2$, . . . $F_n$ at a free bone edge of the intact bone section. Changing includes compression, enlargement, and distortion. This is to be provided since the bone fragment F may not necessarily be at the same level as the intact bone and may be enlarged or reduced thereby. Since this is statically the normal case, fragment changing processing may always be carried out. Once the algorithm has detected a matching bone segment F, the segment is marked specifically. Now, the fragment matching algorithm 3 begins with a further free bone segment $F_1$, $F_2$, . . . , and attempts to place this on the bone edge expanded in the meantime. Should no matching part be able to be found, a match threshold value may be set, which specifies the degree of match that is to be obtained. It may be that a few bone splinters have splintered off at the edge of a piece of bone, and thus, a hundred-percent match is not possible.

At the end, all matching bone fragments F may be found and marked. These may be operatively placed and fixed in an order suggested by the fragment-matching algorithm 3 as a type of "workflow suggestion" for the surgeon. Fragments not able to be assigned (e.g., the splinter fragments<1 $mm^2$) are separately marked (e.g., in color) and may, if necessary, be operatively removed by the surgeon.

The fragment matching algorithm 3 functions based on the recognition of geometrical shapes. Depending on the embodiment, a two or three-dimensional pattern recognition may be carried out here. In alternate forms of embodiments, a database DB is used, in which the anatomical structures are contained. This is helpful in the event of complex fractures. In one embodiment, the database DB may be embodied as a self-learning system and may be able to be expanded by feedback in order thus to improve the quality.

It has been shown in puzzle research that the best results are achieved when the background is colored white, for example, and all puzzle pieces are in one color (e.g., black). Therefore, in an embodiment, there is provision for at least one image change measure $1a$ (e.g., coloring-in) to be carried out. This may be done easily through the automatic segmentation 2, but is an optional feature of the present embodiments. An important difference from the puzzle solutions is to be seen in the different thickness of the bone fragments. Puzzle pieces may be of the same thickness, but bone fragments may rarely be of the same thickness. Therefore, there is provision in one form of embodiment for deriving further information from a different grayscale representation that is correlated with a corresponding different thickness of the bone at different points, and providing this as part of the result data. A curvature value of the bone fragment may also be used for positioning. With the aid of the database DB, the TARGET position may be calculated while taking into consideration the curvature value (e.g., it may be detected how the fragment is to be turned and positioned).

Figure 2:
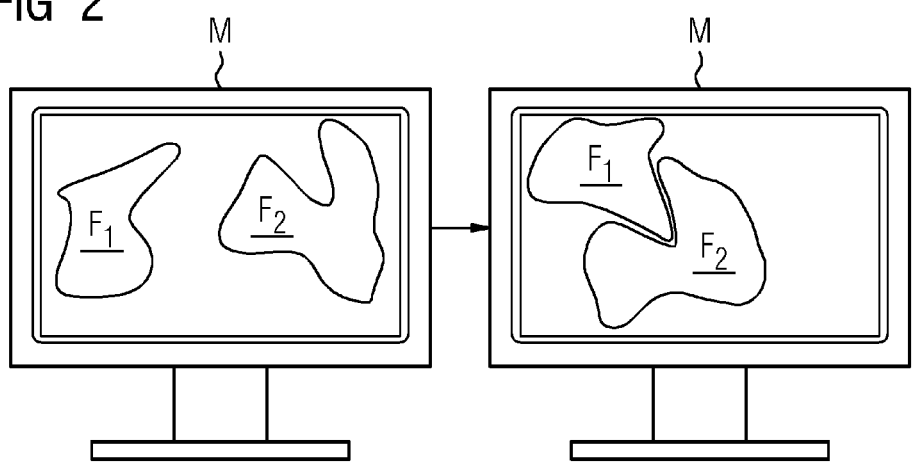
FIG. 2 shows an example of a schematic part diagram of calculated result data on a display device in accordance with an embodiment.

As shown in FIG. 2, a calculated positioning suggestion in the form of result data is shown on the monitor M. The original individual fragments $F_1$, $F_2$, which are shown in FIG. 2 on the left-hand side, are positioned through corresponding spatial changes of location so that the individual fragments $F_1$, $F_2$ match one another. A result or part result of the fragment-matching algorithm 3 is then output on the monitor M (shown in FIG. 2 on the right-hand side).

A control module S serves to execute the fragment-matching algorithm 3 and is a new and unique tool especially for facial surgery, which makes it easier in advance of an operation for the surgeon to carry out complex reconstructions (e.g., restoration) significantly more quickly, more effectively, and more conveniently.

Figure 4:
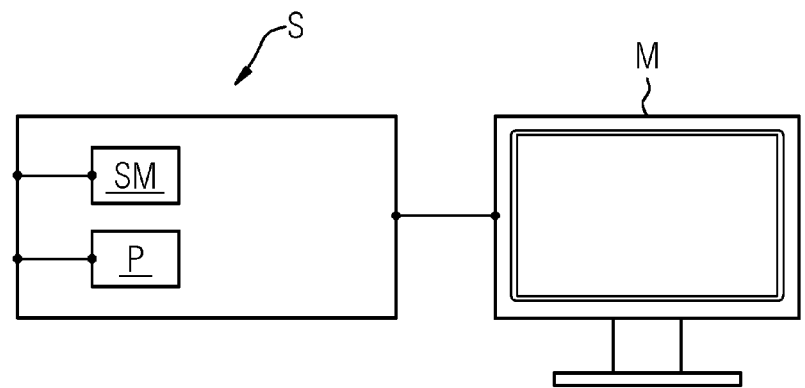
FIG. 4 shows a schematic diagram of one embodiment of a control module with a connected monitor.

As shown in FIG. 4, the control module S includes a segmentation module SM that is intended to apply the segmentation method to the captured image for identification of the bone fragments F contained in the image. The control module S further includes a processor P that is configured to execute the fragment-matching algorithm 3 on the segmented bone fragments for calculation of result data, which contains instruction data for assembling at least one part of the bone fragments F. The control module S exchanges data with the monitor M, which is configured to output 4 the result data in a configurable format. The control module S may be integrated into a computer C or into a computer system. In other forms of embodiments, the processor P is also configured to carry out further tasks, such as, for example, to carry out image processing tasks in order to simplify calculation (e.g., coloring-in, edge processing, pattern recognition procedures, etc.).

The fragment-matching algorithm 3 may be applied in the medical field in principle to all fractures, consisting of at least two individual parts, and also to other fields outside maxillofacial surgery. This field is, however, therefore a typical application, since this application is on the most difficult to reconstruct region of the body, since the facial and cranial bones, because of thin wall thickness and the radii of curvature, are very challenging for reconstructions.

In an embodiment, the result data includes instruction data, which includes a sequence of instructions as a type of recipe as to the order in which the bone fragments F are best to be assembled, before the actual operation is carried out.

In accordance with one aspect, a size threshold value may be entered. The size threshold value identifies a minimum fragment size that is still to be taken in consideration for the execution of the fragment-matching algorithm 3. In practice, this provides that all smaller fragments (e.g., smaller than 2-4 mm$^2$) are no longer repositioned, but are removed.

In accordance with a further aspect, the recording of the image may be repeated after a part of or the entire repositioning process is concluded, in order to increase the accuracy and/or in order to check whether the actual positioning coincides with the calculated TARGET positioning.

Figure 3:
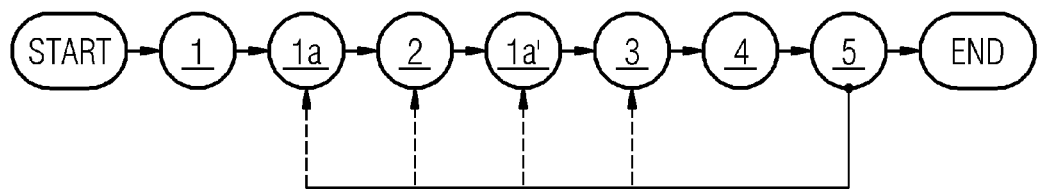
FIG. 3 shows a flow diagram in accordance with an embodiment of a method.

A typical execution in accordance with a form of embodiment is explained in greater detail below in conjunction with FIG. 3.

After the start of the method, medical imaging is carried out in act 1. In the imaging, digital images, in which all or selected bone fragments F are shown, are captured. In act $1a$, an image processing measure may be applied to the captured image, such as, for example, the coloring-in of the fragment F and/or of the background. In act 2, the segmentation method is applied to the captured image in order to identify the individual fragments F shown in the image. Facultatively, a further image process may again be carried out in order to enable the fragment-matching algorithm 3 to be executed even more efficiently. This may include the rotation of the respective bone fragment F in all 3 spatial axes, size changes such as compressions, and enlargements of the fragment F. This is indicated in FIG. 3 with the reference character $1a'$. Then, in act 3, the fragment-matching algorithm 3 is executed for calculating the result data, which is then subsequently displayed in act 4 on the monitor M. This may be done, for example, in the manner as is shown in FIG. 2 on the right-hand side. As shown in FIG. 3 by the dashed lines, the method or individual method acts may be carried out iteratively. Thus, for example, after the output of the result data, an image changing measure $1a$, the segmentation method 2, a further image changing method $1a'$, and/or the fragment-matching algorithm 3 may be executed again. In act 5, the result data and optionally the instruction data are shown on the monitor M. As shown in FIG. 3, by the four dotted-line arrows pointing upwards, it is to be indicated that even after displaying the result data, one or more image processing measure(s), the segmentation 2, and/or the fragment-matching algorithm 3 may be executed.

The description of the invention and the exemplary embodiments are not basically to be understood as restrictive with respect to a specific physical realization of the invention. All features explained and shown in connection with individual forms of embodiments of the invention may be provided in different combination in the inventive subject matter in order simultaneously to realize advantageous effects.

The area of protection of the present invention is given by the subsequent claims and is not restricted by the features explained in the description or shown in the figures.

For a person skilled in the art, the invention may not only be employed with a mobile C-arm, but also with other imaging devices, such as classical x-ray devices, MRT etc. The components of the control module S may be realized distributed between a number of physical products.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for calculation and output of result data based on at least one medical image that has been captured by an imaging device, the method comprising:
acquiring at least one image with a plurality of bone fragments in a digital format, the acquiring comprising carrying out a medical imaging method using the imaging device;
identifying, by a processor, the plurality of bone fragments contained in the at least one acquired image, the identifying comprising using a segmentation method based on the at least one acquired image to provide segmented bone fragments, and verifying the segmentation method by accessing a database in which anatomical structures and part structures are stored, wherein the anatomical structures and the part structures are automatically assignable, by a mapping, to the segmented bone fragments;
calculating, by the processor, result data that includes instruction data for assembling at least a portion of bone fragments of the plurality of bone fragments, the calculating comprising fragment-matching the plurality of bone fragments; and
outputting the result data in a configurable format.

2. The method of claim 1, wherein the fragment-matching is based on an automatic recognition of geometrical shapes.

3. The method of claim 1, wherein the fragment-matching is based on pattern recognition.

4. The method of claim 3, wherein the pattern recognition comprises curve-matching.

5. The method of claim 1, further comprising detecting a matching threshold value that specifies a degree of matching between the plurality of bone fragments.

6. The method of claim 1, further comprising successively expanding the database, the successively expanding comprising automatically storing all captured images, segmented bone fragments, result data, feedback data, or any combination thereof in the database.

7. The method of claim 1, further comprising recalculating the at least one acquired image, the recalculating comprising executing an image processing measure to base the fragment-matching on the at least one image.

8. The method of claim 1, further comprising displaying, by a monitor, the result data.

9. The method of claim 1, further comprising:
detecting a position of a surgical device; and
outputting a signal as the instruction data to provide guidance for movement of the surgical device based on the detected position.

10. A controller configured to calculate and display of result data based on at least one medical image that has been captured by an imaging device in a digital format, a plurality of bone fragments being displayed in the at least one captured medical image, wherein the controller is configured to:
segment the at least one captured medical image for identification of the plurality of bone fragments contained in the at least one medical image to provide segmented bone fragments;
access a database having anatomical structures and part structures, wherein the anatomical structures and the part structures are automatically assignable, by a mapping, to the segmented bone fragments;
calculate result data, the calculation of the result data comprising fragment-matching the plurality of segmented bone fragments, the result data comprising instruction data for assembling at least a part of the bone fragments; and
exchange data with an output unit configured to output the result data in a configurable format.

11. In a non-transitory computer-readable storage medium that stores instructions executable by a digital computer to calculate and output result data based on at least one medical image that has been captured by an imaging device, the instructions comprising:
acquiring at least one image with a plurality of bone fragments in a digital format, the acquiring comprising carrying out a medical imaging method using the imaging device;
identifying, by a processor, the plurality of bone fragments contained in the at least one acquired image, the identifying comprising using a segmentation method based on the at least one acquired image to provide segmented bone fragments, and verifying the segmentation method by accessing a database in which anatomical structures and part structures are stored, wherein the anatomical structures and the part structures are automatically assignable, by a mapping, to the segmented bone fragments;
calculating, by the processor, result data that includes instruction data for assembling at least a part of the plurality of bone fragments, the calculating comprising fragment-matching the plurality of bone fragments; and
outputting the result data in a configurable format.

12. The non-transitory computer-readable storage medium of claim 11, wherein the fragment-matching is based on an automatic recognition of geometrical shapes.

13. The non-transitory computer-readable storage medium of claim 11, wherein the fragment-matching is based on pattern recognition.

14. The non-transitory computer-readable storage medium of claim 13, wherein the pattern recognition comprises curve-matching.

15. The non-transitory computer-readable storage medium of claim 11, further comprising:
detecting a matching threshold value that specifies a degree of matching between the plurality of bone fragments.

* * * * *